(12) United States Patent
Quinlin et al.

(10) Patent No.: US 7,045,635 B2
(45) Date of Patent: May 16, 2006

(54) PROCESS FOR THE SYNTHESIS OF 4-AMINO-4H-1,2,4-TRIAZOLE

(75) Inventors: William T. Quinlin, Amarillo, TX (US); Dillard M. Cates, Amarillo, TX (US)

(73) Assignee: BWXT Pantex, LLC, Amarillo, TX (US)

( * ) Notice: Subject to any disclaimer, the term of this patent is extended or adjusted under 35 U.S.C. 154(b) by 176 days.

(21) Appl. No.: 10/765,342

(22) Filed: Jan. 27, 2004

(65) Prior Publication Data

US 2005/0165241 A1    Jul. 28, 2005

(51) Int. Cl.
*C07D 249/08*    (2006.01)
(52) U.S. Cl. .................................... 548/264.8
(58) Field of Classification Search ............. 548/265.6, 548/264.8
See application file for complete search history.

(56) References Cited

U.S. PATENT DOCUMENTS

| | | | | |
|---|---|---|---|---|
| 5,099,028 A | * | 3/1992 | Goe et al. ................ | 548/265.6 |
| 6,040,456 A | * | 3/2000 | Bourdauducq ........... | 548/265.6 |
| 6,504,033 B1 | * | 1/2003 | Bourdauducq ........... | 548/265.6 |
| 6,509,473 B1 | * | 1/2003 | Drake ..................... | 548/262.2 |

* cited by examiner

*Primary Examiner*—Kamal A. Saeed
*Assistant Examiner*—Susannah L. Chung
(74) *Attorney, Agent, or Firm*—D. Neil LaHaye

(57) ABSTRACT

An improved process for synthesizing 4-amino-1,2,4-triazole. Hydrazine hydrate solution is mixed into ethyl formate, ethanol, and an acidic ion exchange resin in a condenser. The solution is held at 75 degrees Celsius until no more liquid exits the condenser. The solution is then heated to between 130 and 133 degrees Celsius and kept at this temperature long enough to remove water and ethanol and to complete the synthesis. The solution is then cooled to 60 degrees Celsius and filtered to remove the ion-exchange resin. The filtered liquid is then cooled to ambient temperature.

1 Claim, No Drawings

PROCESS FOR THE SYNTHESIS OF 4-AMINO-4H-1,2,4-TRIAZOLE

BACKGROUND OF THE INVENTION

1. Field of the Invention

The invention is generally related to the field of heterocyclic chemistry and the synthesis of nitrogen heterocycles, and more specifically to an improved process for the synthesis of 4-amino-1,2,4-triazole.

2. General Background

The compound 4-amino-4H-1,2,4-triazole (ATA) is important because it can be used to make 1,3,5-triamino-2,4,6-trinitrobenzene (TATB) by the Vicarious Nucleophilic Substitution (VNS) process as set forth in U.S. Pat. No. 5,569,783 to Mitchell, et al. In the VNS reaction, picramide is treated with either hydroxylamine or ATA, which causes the two remaining aromatic hydrogen atoms to be replaced by amine (—NH2) groups. Although ATA produces TATB of better quality than hydroxylamine, ATA is very expensive to purchase ($250/kg). Organic Synthesis, Collective Vol. III describes how to synthesize ATA.

The VNS method is better than the traditional process for TATB because the traditional process used trichlorobenzene, a chlorocarbon compound, as the feedstock. In contrast, the VNS method starts with chlorine-free picramide. Thus, the resulting TATB produced by the VNS method is free of chloride.

U.S. Pat. No. 5,099,028 discloses a method to make ATA. However, the method starts with a carboxylic acid. In the disclosed method 91% formic acid is mixed with 100% hydrazine hydrate and a catalyst, Amberlyst 15 ion exchange resin. Water is distilled off between 105 and 150 degrees Celsius, and the reaction mixture is held at 150 degrees Celsius for six hours. The mixture is then cooled to 80 degrees Celsius, isopropanol is added, the resin is filtered off and rinsed with isopropanol, and the combined filtrates are cooled to precipitate ATA. The slurry is filtered to isolate ATA. Reportedly, the yield is 80%, the purity is 99.5%, and the melting point is between 87 and 89 degrees Celsius. The patent also refers to the use of ethyl formate as a reactant as being undesirable. However, the present invention uses ethyl formate as a reactant with a catalyst such as Amberlyst 15 to produce a satisfactory product at a time and temperature that are within a usable range.

Some of the prior methods require 24 hours for the synthesis of ATA.

SUMMARY OF THE INVENTION

The invention addresses the above problems. What is provided is an improved process for the synthesis of 4-amino-4H-1,2,4-triazole. Hydrazine hydrate solution is mixed into ethyl formate, ethanol, and an acidic ion exchange resin. The solution is held at 75 degrees Celsius until a specific result is observed. The solution is then heated to between 130 and 133 degrees Celsius and kept at this temperature long enough to remove water and ethanol and to complete the synthesis. The solution is then cooled to 60 degrees Celsius and filtered to remove the ion-exchange resin. The resulting liquid is then cooled to ambient temperature.

DETAILED DESCRIPTION OF THE PREFERRED EMBODIMENT

The invention is directed to an improved process for the synthesis of 4-amino-4H-1,2,4-triazole derivatives having the formula

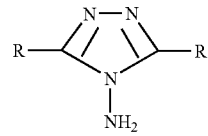

wherein R is hydrogen or an alkyl group containing from 1 to about 10 carbon atoms, which alkyl group can be additionally substituted by one or more aryl, heteroary, hydroxy, or alkenyl substituents The improvement provided by the invention is based on a two-step procedure.

In the first step, ethyl formate is reacted with hydrazine hydrate solution, ethanol, and an acidic ion exchange resin in a condenser. The preferred acidic ion exchange resin is sulfonated cross-linked polystyrene, which is marketed under the trademark Amberlyst 15 by the Rohm & Haas Company. The solution is held at 75 degress Celsius until no more liquid exits the condenser. For ease of reference, the remainder of the description will refer to the use of the Amberlyst 15 ion exchange resin. However, it should be understood that any ion exchange resin having the same formula and the same properties should be suitable for use in the improved process of the invention. Sulfonated cross-linked polystyrene is an acidic macroreticular resin that is thermally stable to 150 degrees Celsius and is usable as an aqueous catalyst.

In the second step, the solution is then heated to between 130 and 133 degrees Celsius and held at this temperature to remove water and ethanol by-products and complete the synthesis of ATA. The solution is then cooled to 60 degrees Celsius and filtered to remove the ion-exchange resin. The resulting liquid is then cooled to ambient temperature.

During experiments to prove the concept, the preferred process used a rotary evaporator comprised of a 1,000-ml, glass, vacuum flask immersed in an oil bath and connected to a water-cooled condenser. Using vacuum, the hazardous reactant, hydrazine, was drawn into the reactor through the condenser from a bottle connected to the upper end of the condenser by a plastic tube. The rotary evaporator proved better than using a 3-necked flask because the operators were not exposed to the hydrazine and the reaction time was shortened because the water and ethanol by-products could be removed more rapidly than when using a 3-necked flask.

The synthesis, using the rotary evaporator, was as follows: Into the rotary evaporator, 116.5 ml hydrazine hydrate solution (99 ml of 99% hydrazine with 17.5 ml water added) was mixed slowly with slight vacuum and agitation into 163 ml ethyl formate, 150 ml ethanol, and 9.6 g Amberlyst 15 (wet) ion exchange resin. The solution was held at 75 degrees Celsius for three hours under slight vacuum until no more liquid exited the condenser. The solution was then heated to between 130 and 133 degrees Celsius under slight vacuum and kept at temperature for three more hours to remove water and ethanol and to complete the synthesis of ATA. The solution was then cooled to 60 degrees Celsius and filtered to remove the ion-exchange resin. The resulting liquid was cooled to ambient temperature, resulting in 55.3 g of white ATA crystals.

There are several advantages to the inventive process. The synthesized ATA was analyzed by high-pressure liquid chromatography (HPLC) employing an NH2 column (25 cm×4.6 mm with 5 micron packing) and a mobile phase of 98% acetonitrile and 2% water at a flow rate of 1 ml/minute and 35 degrees Celsius. The detector was set at 21 nm. The analysis showed that the purity of the synthesized ATA using the Amberlyst 15 ion exchange resin was 83%. Without the ion exchange resin, the purity is 78%. The yield, as a percentage of theoretical was 55% using the ion exchange resin and 56% without the ion exchange resin. The total time for synthesis using the ion exchange resin was six hours, while the total time without the ion exchange resin is twenty-four hours.

Another advantage of the process is that the ion exchange resin can be used twice. The purity of the ATA may not greatly affect the purity of the resulting TATB. However, using ATA with a higher purity means that less is necessary to achieve a stoichiometric amount of the active reagent when making TATB. Another advantage of the process is that the cost of the ion exchange resin is readily offset when comparing the cost of commercially-available ATA to that produced by the inventive process.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A process for synthesizing 4-amino 4H-1,2,4-triazole, comprising the steps:
   a. reacting ethyl formate with a solution of hydrazine hydrate solution, ethanol, and sulfonated cross-linked polystyrene ion exchange resin in a condenser;
   b. maintaining the mixture at a temperature of 75 degrees Celsius until no more liquid exits the condenser;
   c. heating the solution to a temperature of approximately 130 to 133 degrees Celsius;
   d. maintaining the solution at the temperature of step c for a sufficient time to remove ethanol and water and complete the synthesis of the 4-amino 4H-1,2,4-triazole;
   e. cooling the solution to 60 degrees Celsius;
   f. filtering the solution to remove the ion exchange resin; and
   g. cooling the filtered liquid to ambient temperature.

* * * * *